US006042602A

United States Patent [19]

Wells

[11] Patent Number: 6,042,602

[45] Date of Patent: Mar. 28, 2000

[54] APPARATUS FOR EFFECTING TRACTION ON THE SPINE AND METHOD OF USING THE SAME

[76] Inventor: Charles A. Wells, 1207 Fleming Rd., Cordele, Ga. 31015

[21] Appl. No.: 09/087,805

[22] Filed: Jun. 1, 1998

Related U.S. Application Data

[60] Provisional application No. 60/050,627, Jun. 4, 1997.

[51] Int. Cl.[7] ........ A61F 5/00

[52] U.S. Cl. ........ 606/241; 482/111; 482/93; 482/92

[58] Field of Search ........ 606/241; 482/92, 482/93, 105, 111, 907; 602/32, 36, 38; 601/5, 23, 33, 156, 157, 160, 166; 4/573.1, 574.1, 575.1, 621; 441/106, 108, 110–114, 129; 607/77, 81, 85

[56] References Cited

U.S. PATENT DOCUMENTS

| | | | |
|---|---|---|---|
| 3,859,990 | 1/1975 | Simon . | |
| 4,181,124 | 1/1980 | Pauletich | 601/157 |
| 4,722,329 | 2/1988 | Kalvåg . | |
| 5,033,460 | 7/1991 | Goldish . | |
| 5,078,126 | 1/1992 | Perry . | |
| 5,092,589 | 3/1992 | Packer | 482/92 |
| 5,105,804 | 4/1992 | Van Nostrand . | |
| 5,258,018 | 11/1993 | Van Nostrand . | |
| 5,409,412 | 4/1995 | Colon | 441/129 |

FOREIGN PATENT DOCUMENTS

| | | | |
|---|---|---|---|
| 2395749 | 3/1979 | France | 607/85 |
| 1607217 | 12/1969 | Germany | 607/85 |

*Primary Examiner*—Richard J. Apley
*Assistant Examiner*—Lori Baker
*Attorney, Agent, or Firm*—Pillsbury Madison & Sutro LLP

[57] ABSTRACT

An apparatus for effecting spinal traction on a patient includes a tub containing liquid in which a patient, buoyantly supported by a floatation device, can float in a generally upright position in a state of buoyant equilibrium. The level of the liquid in the tub can be varied, which effects a variation on a traction force acting on the patient as the floatation device seeks new positions of buoyant equilibrium in response to the change in liquid level. The traction force may be generated by one or more weighted devices worn on the body of the patient or by a harness attached to the patient and secured within the tub to resist upward movement of the patient when the liquid level rises in the tub. The liquid level within the tub is varied by a liquid level varying apparatus associated with the tub which operates generally by displacing a volume of liquid within the tub to vary the level of the liquid by an amount corresponding to the volume of displaced liquid. A method for effecting spinal traction includes floating a patient in a vessel of water, applying a body-tensioning force to the patient's body, and raising and lowering the level of liquid in the vessel to effect variations in the body-tensioning force as the patient's floating body seeks a new position of buoyant equilibrium.

25 Claims, 5 Drawing Sheets

APPARATUS FOR EFFECTING TRACTION ON THE SPINE AND METHOD OF USING THE SAME

This application claims the benefit of prior filed provisional application No. 60/050,627, filed Jun. 4, 1997.

FIELD AND BACKGROUND OF THE INVENTION

The present invention relates to a method and apparatus for therapeutically treating spinal discomfort and injury.

The human spinal column comprises a series of vertebral blocks extending from the occiput to the sacrum, or tailbone. The individual vertebra are united by longitudinal ligaments and by intervertebral discs disposed between laminae of cartilage. The spinal vertebra house the spinal cord and provide intervertebral outlets through which pass spinal nerves extending from the spinal cord.

Misalignment of the vertebra or degeneration of the intervertebral discs, combined with compression of the spinal column from the weight of the upper body, can result in pinching and impingement of the spinal nerves. Pinching of the nerves can cause pain and impingement can interfere with the flow of neurological impulses, which can lead to various muscular disabilities. Such spinal discomfort has been treated using traction, which is the technique of applying tension to the spinal column to decompress the spinal column and open the intervertebral disc spaces and/or to permit realignment of the vertebra. With the intervertebral disc spaces opened and with the vertebra realigned, pinching or impingement of the spinal nerves is alleviated, thus reducing pain and restoring the normal flow of neurological impulses. Typically, traction is applied by applying a tensile force, generated by weights with ropes and pulleys, to a patient's lower body by means of some type of harness and holding an upper portion of the patient's body stationary, thus placing the spinal column in a state of tension.

The benefits of performing muscular and skeletal rehabilitation on a patient while the patient is at least partially immersed in warm water have been recognized. Warm water relaxes muscles and assists in facilitating bodily articulations. Moreover, the buoyancy of water reduces the gravitational weight load on the patient's spine and joints. For these reasons neurosurgeons and orthopedists have recently begun prescribing joint and spinal rehabilitation to be performed with the patient in a warm pool. The benefits of applying traction while the patient's body is immersed in warm water also have been recognized. Indeed, the prior art literature describes different traction methods which are performed on a patient immersed in water.

For example, U.S. Pat. Nos. 5,105,804 and 5,258,018 to Van Nostrand disclose an apparatus and method whereby traction is applied to a patient floating in water in a spa that is deep enough so that the patient's feet do not touch the bottom of the spa when the patient is in a generally upright posture. Floatation devices are placed around the patient under the arm and/or around the neck, and weights are attached to the patient's legs or hips. The weights, acting in a direction generally opposite to the direction of the buoyant force of the floatation devices, place the patient's spine in a state of tension as the patient floats in the spa. The patient can remain stationary with the static load of the weights stretching the spine, or the patient can perform leg, arm, and hip-flexing exercises while floating in the spa.

U.S. Pat. No. 5,078,126 to Perry also discloses a method whereby traction is applied to a patient partially submerged in a water pool. The patient is suspended generally vertically within the water pool by means of a support frame above the patient to which is attached a harness which holds up the patient by the head and neck and/or by a floatation device, such as an inflatable vest. Weight is attached by means of a tether to the patient's hips and neither the weights nor the patient's feet are permitted to touch the bottom of the pool. Accordingly, the patient's spine is in a state of tension.

In the prior art traction methods, including those performed while the patient is partially immersed in a pool, the spinal traction force is a static force. That is, the patient's spine is subjected to a constant tensile force that does not vary. Where the traction force is static, relatively large loads can be required to achieve the desired spinal decompression. Loads of up to 70 pounds are not unheard of and the Van Nostrand patents discussed above call for loads of 10 to 20 pound buoyant weight. Such large weights can be awkward and uncomfortable to the patient and can lead to injury if improperly used.

By applying dynamic traction; that is, by subjecting the spine to tensile forces that vary between minimum and maximum extremes, certain benefits can be realized. Dynamic loads can produce therapeutic effects employing external traction loads of small magnitude compared with those used with static traction techniques. In addition, dynamic traction can set the spine in motion and effect dynamic spinal adjustments to alleviate spinal discomfort. The prior art traction techniques, however, do not provide for the application of dynamic traction, and therefore, these benefits have heretofore gone unrealized.

SUMMARY OF THE INVENTION

It is an object of the present invention therefor to provide an apparatus and method whereby the therapeutic benefits of dynamic spinal traction and the benefits of treatment performed on a patient submerged in a liquid are combined to achieve improvements in treatment of spinal injury and discomfort.

This object is achieved by an apparatus for effecting traction on a spinal column of a patient which comprises a vessel containing liquid at a level sufficient to float at least one patient therein; a floatation device to be engaged with a portion of the body of a patient for creating a buoyant force for buoyantly supporting the patient in the liquid contained in the vessel; and a liquid level varying mechanism associated with the vessel. The liquid level varying apparatus is constructed and arranged to raise and lower the level of the liquid within the vessel so as to effect variations of a traction force exerted on the patient's body by the buoyant force created by the floatation device and a second force acting in a direction opposite to the direction of the buoyant force as the floatation device responds to variations in the level of the liquid within the vessel by seeking new buoyant equilibrium positions within the liquid for each variation in the level of the liquid within the vessel.

This object is also achieved by a method for effecting traction on a spinal column of a patient which comprises placing the patient in a vessel containing liquid at a level sufficient to float at least one patient therein, engaging a floatation device with the body of the patient for creating a buoyant force for buoyantly supporting the patient in the liquid contained in the vessel, applying a body-tensioning force to the patient's body, the body-tensioning force having a component acting in a direction opposite to the buoyant force created by the floatation device, and raising and lowering the level of the liquid within the vessel so as to effect variations of the body-tensioning force exerted on the patient's body as the floatation device responds to variations in the level of the liquid within the vessel by seeking new buoyant equilibrium positions within the liquid for each variation in the level of the liquid within the vessel.

Other objects, features, and characteristics of the present invention will become apparent upon consideration of the following description and the appended claims with reference to the accompanying drawings, all of which form a part of the specification, and wherein like reference numerals designate corresponding parts in the various figures.

DESCRIPTION OF THE PRESENTLY PREFERRED EMBODIMENT

Figure 1:
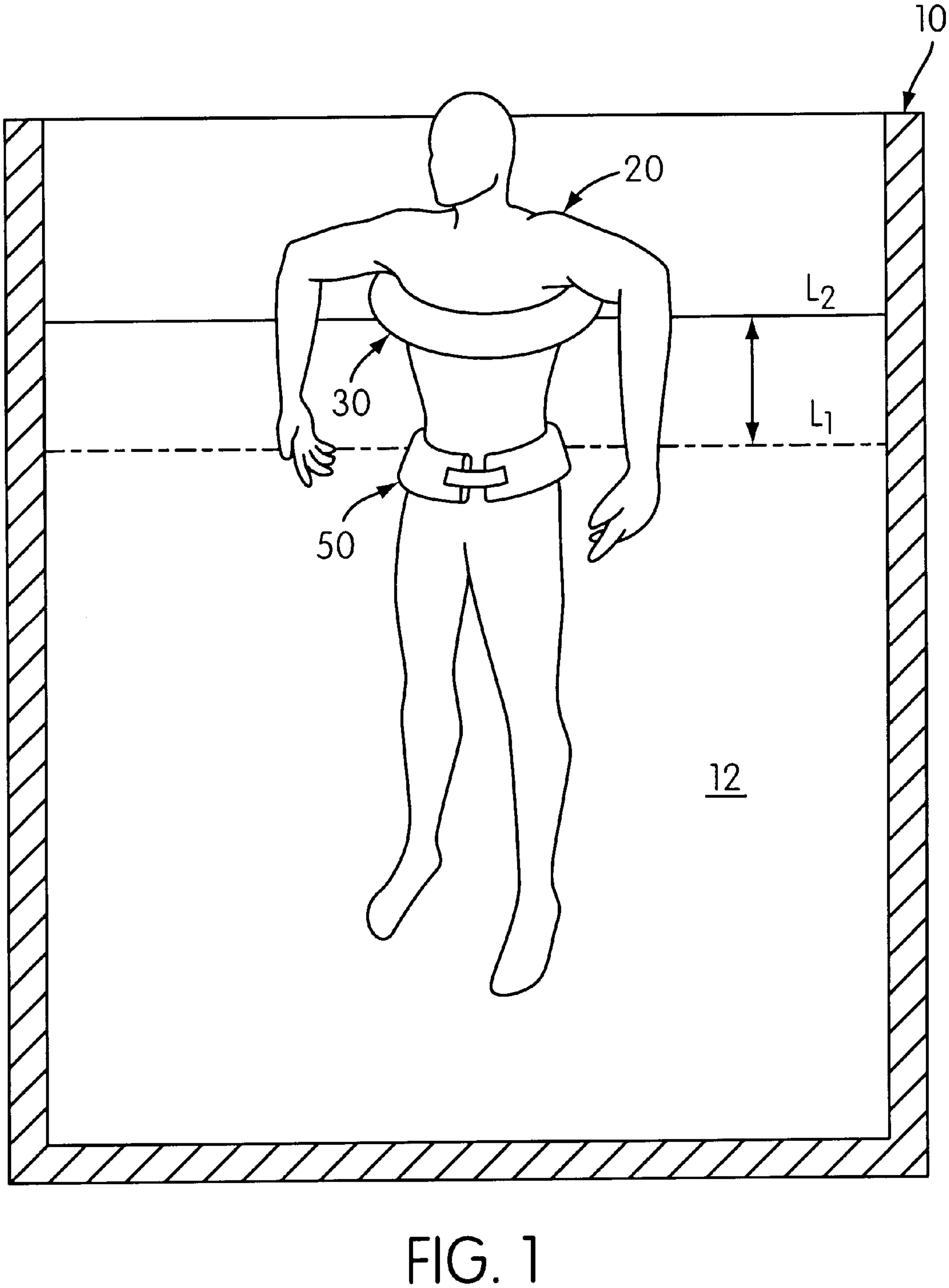
FIG. 1 is a view, partially in cross section, of a patient floating in a therapeutic tub which illustrates aspects of the present invention.

Illustrating aspects of the therapeutic apparatus and method of the present invention, there is shown in FIG. 1 a patient 20 floating in a liquid 12, preferably water, contained within a vessel, such as tub 10. The temperature of the liquid in the tank is preferably maintained at or slightly below normal human body temperature, i.e., between 95° F. and 98° F. The patient 20 is supported within the liquid 12, preferably in a state of buoyant equilibrium, by means of an underarm floatation device 30. A weighted belt 50 is worn around the hips of the patient 20. The weight of the belt 50 acts downwardly under the force of gravity, opposite to the upward buoyant force created by the floatation device 30. Accordingly, the effect of the weighted belt is to produce a therapeutic decompressing traction force on the patient's spine. It can be appreciated that therapeutic traction forces can be applied to other areas of the body by suitably applied weights such as at the thighs, calves, ankles, and/or feet of the patient. In addition, the traction applied to the spinal column can be limited to an upper portion of the spine simply by moving the weight belt 50 further up the patient's torso.

It is a feature of the present invention to exploit the therapeutic effects of applying a dynamically varying traction force obtained by raising and lowering the water level between levels L1 and L2 while a patient 20 is suspended within the liquid 12 by means of the floatation device 30 with weights attached at desired portions of the body. The inertial forces of weights attached to the patient's body caused by the raising and lowering of the liquid level applies a gentle dynamic stretching impulse force to the body part to which the weight is attached. More specifically, as illustrated in FIG. 1, with the patient 20 floating at level L2 the weight belt 50 applies a constant decompressing force to the patient's spine. If the liquid level is then dropped to level L1 at a sufficient rate, the traction force exerted by the weight 50 will first be temporarily partially relieved because of the at-rest inertia of the weight belt 50 as the patient 20 accelerates downward from level L2 toward level L1 as the floatation device 30 seeks a new buoyant equilibrium position. When the liquid level reaches level L1 and the liquid level stops falling, the patient's fall will stop rapidly as the floatation device 30 achieves a new buoyant equilibrium. The weight 50, having developed a downward momentum of its own, will impart a gentle impulsive traction force to the patient's spine when the weight's fall is stopped by the floating patient. It is this impulsive force applied by the weight due to the change in water level that provides certain therapeutic benefits. When the water level is again raised from level L1 to level L2, a second downwardly directed impulsive traction force can be generated when the water level is raised, caused by the inertial resistance of the weight as it changes from an at-rest state to an upwardly moving state as the floatation device again seeks a new position of buoyant equilibrium at level L2.

Accordingly, a weight attached to a portion of the patient's body will impart a gentle impulsive traction force to the patient's floating body when the patient's body is raised and lowered with the liquid level as the floatation device seeks new positions of buoyant equilibrium and the weight changes from a downwardly moving state to an at-rest state and from an at-rest state to an upwardly moving state. The size of the dynamic traction impulses can be controlled by the amount and rate of liquid level change. The amount and rate of the liquid level rise and fall can be tailored to the specific patient requirements and therapeutic effects desired. Rise and fall of any length may be employed, although it is presently contemplated that a rise and fall of 12 inches will create significant therapeutic benefits. In addition, the rise and fall of the water can be effected in a periodic manner to provide a dynamically varying traction force. The frequency of the periods of rise and fall can be tailored to the patient and the injury being treated.

Various pieces of equipment for use in the method of the present invention are shown in FIGS. 2–9.

Figure 2:
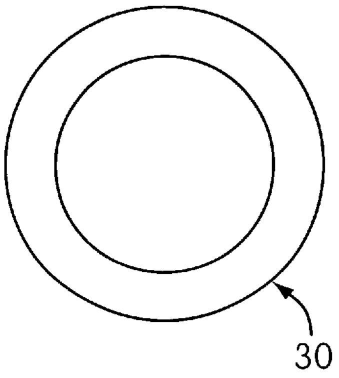
FIG. 2 is a plan view of an underarm floatation device for use in the present invention.
Figure 3:
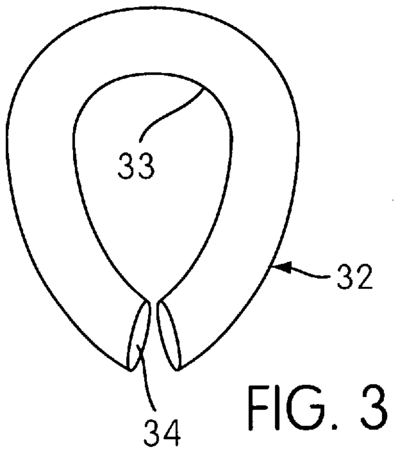
FIG. 3 is a plan view of a floatation collar for use in the present invention.

Shown in FIG. 2 is an underarm floatation device 30 in the shape of an annulus, which may comprise an air-filled innertube or a solid structure formed of a buoyant material, such as expanded rigid polystyrene plastic. Shown in FIG. 3 is a floatation collar, or yoke 32, which may also be inflatable or formed from a buoyant material, such as expanded rigid polystyrene plastic. The collar can be worn around the patient's neck so as to support the patient's head above the liquid level. An opening 34 is provided in the collar 32 so that the collar can be slipped over the patient's neck, because the opening 33 in the collar is typically smaller than the size of a patient's head so that the patient's head will not slip through the collar. Fasteners (not shown) may be provided across the opening 34 for securing the collar 32 to a patient's neck. Other types of floatation devices, which are not shown, but which may be used in the therapeutic tube of the present invention, include floatation vests worn on the torso of the patient and floatation cuffs worn around the upper arms of the patient.

Figure 4:
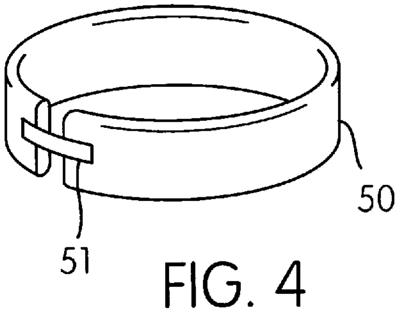
FIG. 4 is a perspective view of a hip weight attachment for use in the present invention.

A variety of weight adding elements for attachment to various portions of a patient's body are shown in FIGS. 4–9. The weight adding elements, when attached to the patient's body, work in conjunction with the floatation device to apply a body-tension to the patient. A weight belt 50 is shown in FIG. 4. As described above with respect to FIG. 1, weight belt 50 is worn around the hips of the patient so as to provide a downward traction force on the patient's hips and spine. Belt 50 preferably includes an attaching clasp 51 for closing the belt around the patient's body.

Figure 5:
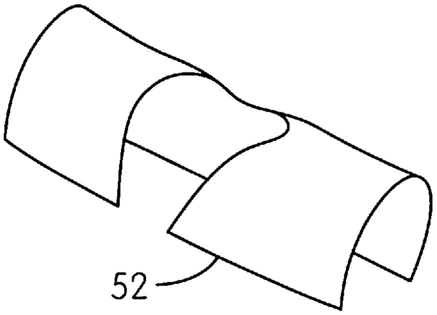
FIG. 5 is a perspective view of a shoulder weight attachment for use in the present invention.

A shoulder weight apparatus 52 is shown in FIG. 5. As can be appreciated from the shape of the device as shown in the figure, the shoulder weight 52 is worn over the shoulders and around the neck of the patient so as to provide a traction force on the patient's neck when the patient's head is supported above the liquid level.

Figure 6:
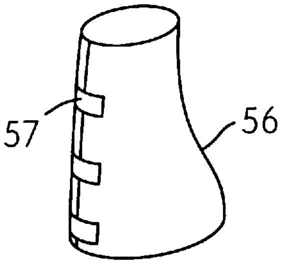
FIG. 6 is a perspective view of a calf weight attachment for use in the present invention.

A calf weight 56 is shown in FIG. 6. Calf weight 56 is sized and shaped to be wrapped around and secured by a plurality of attachment straps 57 around the patient's calf so as to provide a traction force on the patient's knee, thigh, hips and spine. Calf weights can be worn on one or both of the patient's calves depending on the desired therapeutic effect. Straps 57 can include buckles, clasps, or Velcro™ for securing the calf weight 56 in place.

Figure 7:
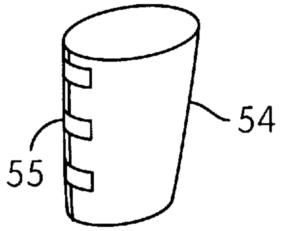
FIG. 7 is a perspective view of a thigh weight attachment for use in the present invention.

A thigh weight 54 is shown in FIG. 7. Thigh weight 54 can be wrapped around the patient's thigh and secured in place by means of a plurality of attachment straps 55. Weight 54 attached to the patient's thigh can produce a traction effect in the thigh, hips, and spine. A thigh weight 54 can be attached to one or both of the patient's thighs, depending on the desired therapeutic effect. Straps 55 can include buckles, clasps, or Velcro™ for securing the thigh weight 54 in place.

Figure 8:
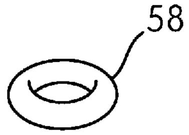
FIG. 8 is a perspective view of an ankle weight attachment for use in the present invention.

An ankle weight 58, shown in FIG. 8, can be attached around the patient's ankles so as to provide traction to the entire leg, hips, and spine of the patient. An ankle weight 58 can be attached to one or both of the patient's ankles depending on the therapeutic effects desired.

Figure 9:
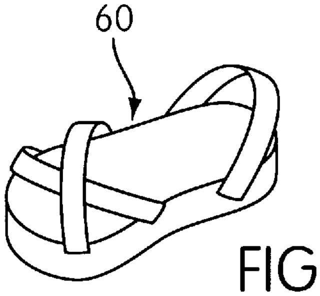
FIG. 9 is a perspective view of a weighted sandal for use in the present invention.

A weighted sandal 60 is shown in FIG. 9. The sandal 60 can be worn on the patient's foot to effect traction to the entire leg (including the ankle), hips, and spine of the patient.

Any amount of weight may be attached to the patient's body employing one or more of the above described weight attaching elements, depending on the patient and the desired therapeutic effect. Because of the advantageous effects of dynamic traction, therapeutic benefits can be realized even if no external weights are attached to the patient. That is, when the patient is buoyantly supported by a floatation device and the liquid level is varied, causing the floatation device to seek new positions of buoyant equilibrium, the weight of the patient's own body below the floatation device, being dynamically cycled, can produce therapeutic benefits for the spine.

Alternate embodiments of the therapeutic tube of the present invention are shown in FIGS. 10 and 11. As in the embodiment of FIG. 1, a patient 20 is buoyantly supported in the liquid 12 contained in the tub 10 by means of a floatation device, such as an underarm floatation device 30. Although the floatation device 30 shown in FIGS. 10 and 11 is an underarm device in the shape of an annulus, other types of floatation device can be used in conjunction with or instead of the underarm device. Other types of floatation devices may include a neck collar, such as neck collar 32 shown in FIG. 3, or a floatation vest (not shown) to be worn on the torso of the patient 20. Instead of attaching weights to the patient's body below the floatation device 30, however, the patient is held stationary by means of a hip harness secured within the tub 10. In the embodiment of FIG. 10, a hip harness 90 is secured by means of flexible tether straps 92 to anchor rings 94 provided on the walls of the tub 10. Rings 94 could alternatively, or in addition, be provided in the floor of the tub 10. In the embodiment of FIG. 11, a hip harness 96 is secured to an upright rigid post 98 extending up from the floor of the tub 10. Hip harnesses 90 and 96 are preferably wide belts to be worn around the hips of the patient 20. Harnesses which are secured to the legs or the ankles of the patient 20 may be used as well.

Figure 10A:
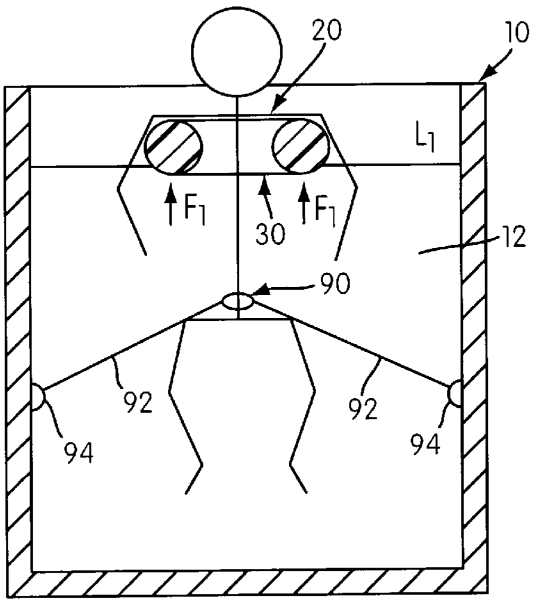
FIGS. 10A and 10B are schematic cross-sectional views of a patient floating in a therapeutic tub, illustrating a first alternate embodiment of the invention.
Figure 11A:
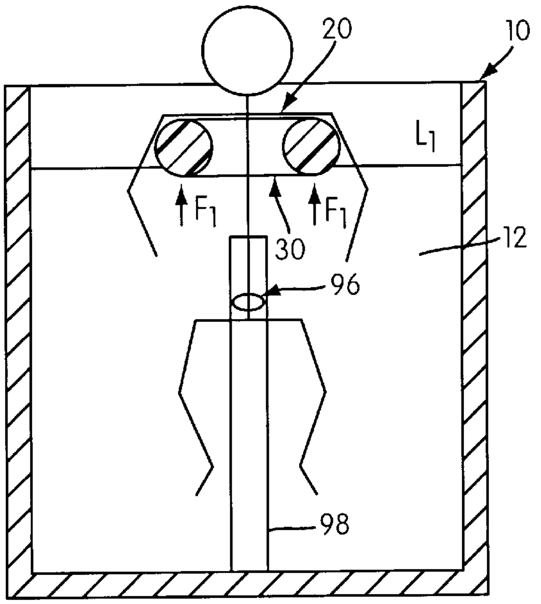
FIGS. 11A and 11B are schematic cross-sectional views of a patient floating in a therapeutic tub, illustrating a second alternate embodiment of the invention.

As shown in FIG. 10A, when the patient 20 is floating in a state of buoyant equilibrium within the tub 10 with the liquid 12 at level L1, the tether straps 92, attached to the hip harness 90, are secured in a taut manner to the anchor rings 94 to resist upward movement of the patient 20 and floatation device 30. The lengths of the tether straps 92 can be adjusted to accommodate patients of various sizes. As shown in FIG. 11A, when the patient 20 is floating in a state of buoyant equilibrium within the tub 10 with the liquid 12 at level L1, the hip harness 96 is attached to the upright post 98 to resist upward movement of the patient 20 and the floatation device 30. To accommodate patients of various sizes, the hip harness 96 is preferably attachable at a plurality of different positions along the upright post 98.

Because the hip harnesses 90 or 96 are secured when the patient is initially in a state of buoyant equilibrium, almost no tension is generated between the harness 90 or 96 and the floatation device 30 except the tension generated by the patient's own weight, and thus, the patient's spine is under only mild traction. In the embodiment of FIG. 11, the harness 96 can be secured to the upright post 98 so as to completely support the patient's weight, so that no tension is generated between the harness 96 and the floatation device 30.

Alternatively, before the hip harness 90 or 96 is secured within the tub 10, the patient 20 and floatation device 30 could be submerged a prescribed distance below buoyant equilibrium by a submerging force, so that after the harness 90 or 96 is secured and the patient 20 and floatation device 30 are released from the submerging force, the patient's spine will be placed in a state of tension as the floatation device 30 seeks buoyant equilibrium against the resistance of the secured harness 90 or 96. As an alternative to a submerging force, an inflatable floatation device can be used and the harness 90 or 96 can be secured when the floatation device is only partially inflated. Spinal traction can be effected by further inflating the floatation device after the harness 90 or 96 is secured, thus causing the floatation device to seek a higher equilibrium position against the resistance of the secured harness 90 or 96.

Figure 10B:
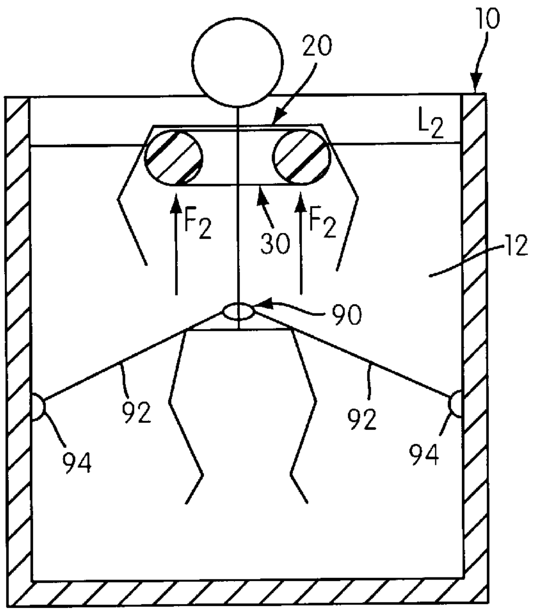
Figure 11B:
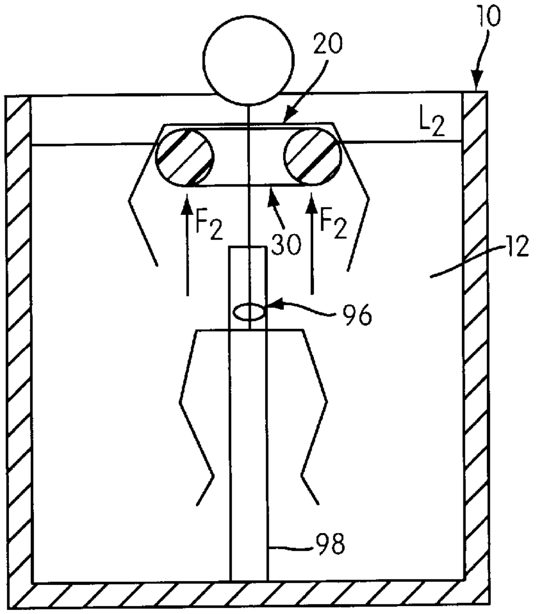

When the patient 20 is floating initially in the tub 10 with the liquid 12 at level L1, a buoyant force F1 created by the floatation device 30 acts upwardly on the patient 20. As described above, the patient's spine may or may not be in a state of traction depending on whether the patient is at buoyant equilibrium with the harness 90 or 96 secured. If the level of the liquid 12 is then raised to level L2, as shown in FIGS. 10B and 11B, the floatation device 30 will seek a higher equilibrium position against the resistance of the secured harness 90 or 96, and the floatation device 30 will create a larger buoyant force F2. Accordingly, the spinal traction force will increase. By oscillating the level of the liquid 12 between levels L1 and L2, the traction force will be dynamically varied between F1 and F2.

Figure 13:
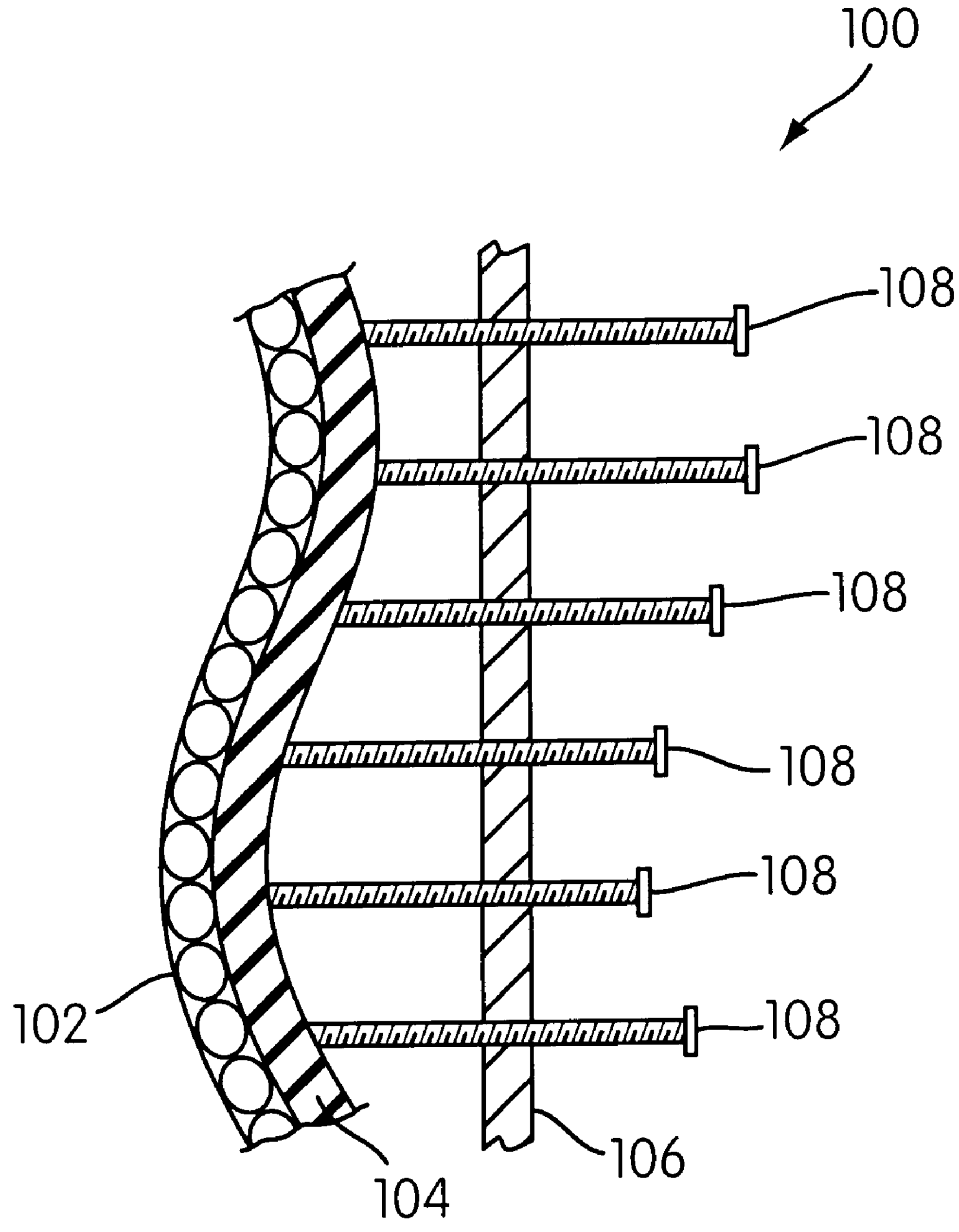
FIG. 13 is a cross-sectional view of a back brace suitable for use in the method of the present invention.

A back brace suitable for use in the method of the present invention is shown in FIG. 13. It is a matter of elementary physics that when opposite ends of a flexible curved object are pulled in opposite directions, the tension will impart a straightening effect to the curved object. Similarly, when a patient is suspended by an upper portion of the body and a weight is suspended from a lower portion of the body, the tension imparted by the buoyancy of the floatation device and the weight effects a straightening, as well as a decompressing, force to the patient's spine. To help maintain the spine's desired curvature, an adjustable brace 100 is provided.

The brace 100 comprises an elongated plate member 106 preferably made of a strong light-weight material, such as aluminum, having a plurality of threaded adjusting pins 108 extending transversely therethrough. An elongated pad 104, preferably comprised of a flexible material such as rubber, is disposed at the ends of the adjusting pins 108.

The brace 100 is positioned against the patient's spine 102 and is held in place by a corset or vest (not shown) extending around the patient's torso. Each of the adjusting pins 108 is selectively turned in or out to place the portion of the pad 104 at the end of the pin in contact with the spine 102. As can be appreciated from FIG. 13, by properly adjusting all of the pins, the pad 104 will be made to conform to the spine 102. Thus, a spine-straightening force exerted by a weight suspended from a lower extremity of the patient will be countered by the pad 104 conformed snugly to the curvature of the spine.

Figure 12:
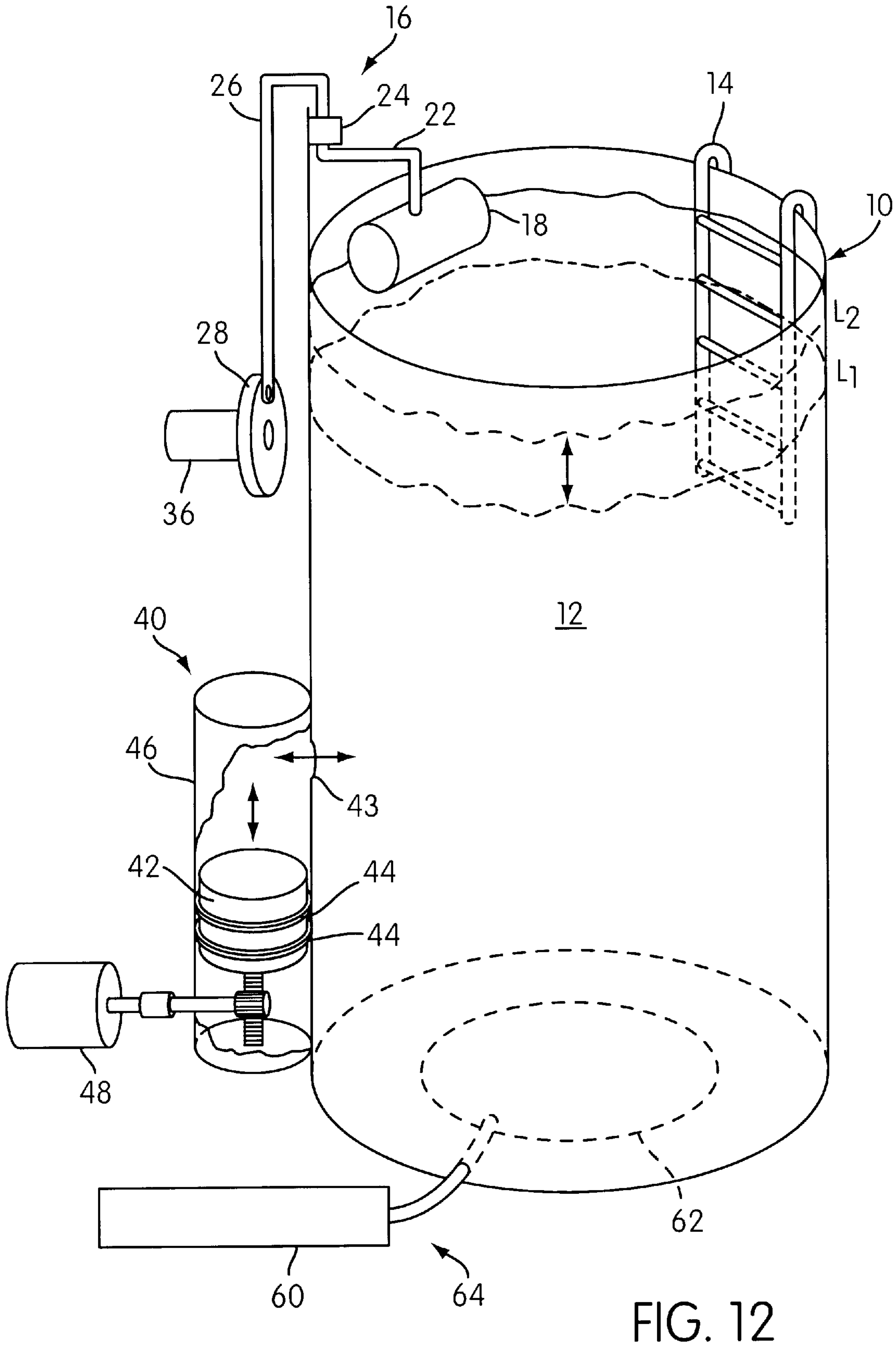
FIG. 12 is a perspective view of a therapeutic tub according to the present invention illustrating various devices for raising and lowering the liquid level within the tub.

Various arrangements for raising and lowering the level of a liquid in a tank are shown in FIG. 12. The liquid containing tub is represented generally by reference No. 10 as in the previous figures. Although tub 10 is shown to be cylindrical in shape, the tub may be of any suitable shape such as rectangular or oval. A ladder 14 or other step structure is preferably provided to assist the patient in entering and exiting the tub 10.

Fundamentally, effecting a level change of the liquid 12 from level L1 to level L2 requires the displacement of a sufficient amount of fluid. There are illustrated in FIG. 12 three alternative devices for effecting such a fluid displacement. Although a therapeutic tub according to the present invention could incorporate more than one of the fluid displacement devices shown, or other mechanisms for effecting fluid level change which are not shown, it is presently contemplated and preferred that, for simplicity and cost management, only one fluid displacement device be incorporated into the therapeutic tub.

A plunger device is indicated generally by reference No. 16. The plunger device 16 includes a drum 18 which may be of a cylindrical shape with closed ends. Drum 18 is connected by a linkage structure 22 which is preferably supported and guided by a guide structure 24 and attached to a jack shaft 26. Jack shaft 26 is attached to drive wheel 28 so as to be eccentric with respect to the center of wheel 28. Wheel 28 is operatively coupled with a driving mechanism, such as motor 36. As wheel 28 rotates, jack shaft 26, pivotally mounted at an outer peripheral edge of gear wheel 28, is caused to alternately rise and fall. By the connection to jack shaft 26 through linkage 22, drum 18 is correspondingly also caused to rise and fall into and out of the liquid 12. It can be appreciated that the level of the liquid 12 will be raised when drum 18 is submerged in the liquid and a volume of liquid equal to the volume of drum 18 is displaced, and the liquid level will fall when the drum 18 is removed from the liquid. Continued rotation of the wheel 28 causes reciprocal motion of the drum 18 into and out of the liquid 12, thus causing a corresponding rise and fall of the liquid.

The rate of the rise and fall of the liquid can be varied by varying the rate of rise and fall of the plunger 18, i.e., by varying the rotational speed of wheel 28. The amount of fluid rise and fall can be varied by varying the volume of fluid displaced by drum 18, e.g. by varying the volume of drum 18 itself and/or by varying the amount of drum 18 that is actually submerged.

A piston device is generally shown at reference No. 40. Piston 42 is reciprocally movable within a piston cylinder 46. Piston 42 preferably includes one or more peripheral seals 44 disposed around the piston 42 so as to create a fluid-tight seal between piston 42 and an inner wall of cylinder 46. Cylinder 46 is in fluid communication, via opening 43, with the tub 10. It can be appreciated that as piston 42 extends upwardly within cylinder 46, a volume of liquid within cylinder 46 is expelled from cylinder 46 and through the opening 43 into the tub 10 to cause the liquid level to rise, and as the piston 42 is contracted downwardly within the cylinder 46, a volume of liquid is drawn from the tub 10 and into the cylinder 46 through opening 43, thus causing the liquid level to fall.

Piston 42 may be driven by any conventional means such as motor 48, which may comprise an electric or hydraulic motor, or the piston 42 may be driven pneumatically by air pressure generated by a compressor 60. The rate of liquid rise and fall can be varied by varying the reciprocating speed of piston 42. Further, the amount of liquid rise and fall can be varied by varying the stroke of piston 42.

A fluid bladder device for displacing an amount of liquid is indicated generally by reference No. 64. A bladder 62 is secured within the tub 10 at a position below the lowest level of the liquid in the tub, preferably at the bottom of the tub 10. Bladder 62 is preferably formed of a durable elastomer, such as rubber. Bladder 62 is connected to a fluid pump 60, such as an air compressor. It can be appreciated that when fluid is pumped into the bladder 62, the liquid in the tub 10 will be displaced in an amount corresponding to the increase in volume of the bladder 62, thus causing the liquid level to rise, and when the fluid is removed from the bladder 62, the liquid level will fall in an amount corresponding to the decrease in volume of the bladder 62.

The rate of liquid rise and fall within tub 10 can be varied by varying the rate at which fluid is pumped into and removed from the bladder 62, and the amount of liquid rise and fall can be controlled by controlling the volume of fluid pumped into the bladder 62.

An inflow and discharge device is represented generally by reference No. 80 in FIG. 12. The device 80 includes an inflow conduit 86 and a discharge conduit 82. Inflow conduit 86 and discharge conduit 82 are connected to one or more pumps (not shown) for providing the necessary positive and negative fluid pressures. Inflow and discharge conduits 86 and 82 may also include valve mechanisms 88 and 84, respectively. The level of the liquid in the tub 10 may be increased by introducing an appropriate amount of liquid from inflow conduit 86 into the tub 10. Similarly, the liquid level may be dropped by discharging an appropriate amount of liquid through the discharge conduit 82. Valves 88 and 84 may be manual valves allowing for the manual adjustment and fluctuation of the liquid level in the tub 10. Alternatively, valves 88 and 84 may be automatically controlled so as to provide automatic and precise liquid level fluctuations.

The rate of liquid rise and fall within the tub 10 can be varied by varying the rate at which the valves 88 and 84 are alternately opened and closed, and the amount of rise and fall can be varied by the amount of liquid introduced into and discharged from the tub 10. The amount of fluid can of course be varied by varying the time each valve is left open and/or by the speed at which the fluid is introduced or discharged, i.e., the amount of pressure (positive and negative) applied to the liquid flowing through the inflow conduit 86 and discharge conduit 82.

It will be realized that the foregoing preferred specific embodiment of the present invention has been shown and described for the purposes of illustrating the functional and structural principles of this invention and are subject to change without departure from such principles. Therefore, this invention includes all modifications encompassed within the spirit and scope of the following claims.

What is claimed is:

1. An apparatus for effecting traction on a spinal column of a patient, said apparatus comprising:

a vessel containing liquid at a level sufficient to float at least one patient therein;

a floatation device to be engaged with a portion of the body of a patient for creating a buoyant force for buoyantly supporting the patient in the liquid contained in said vessel; and means for varying the level of liquid within said vessel by alternately displacing and replacing a volume of liquid within said vessel to alternately raise and lower the mean level of the liquid within said vessel by an amount corresponding to the volume of liquid displaced and replaced so as to effect variations of a traction force exerted on the patient's body by the buoyant force created by said floatation device and a second force acting in a direction opposite to the direction of said buoyant force as said floatation device responds to variations in the level of the liquid within said vessel by seeking new buoyant equilibrium positions within the liquid for each variation in the level of the liquid within said vessel.

2. The apparatus of claim 1 further comprising a body-tensioning device constructed and arranged to be attached to one or more portions of the patient's body and to create the second force on the patient's body having a component acting in a direction opposite to the buoyant force created by said floatation device.

3. The apparatus of claim 2, wherein said body-tensioning device comprises one or more weight elements attached externally to one or more portions of the patients body, the one or more weight elements pulling on the patient's body in directions opposite to the buoyant force created by said floatation device, and wherein the variations of the traction force are created by inertial forces of said one or more weight elements generated as said floatation device and the patient supported thereby rise and fall with the level of the liquid within said vessel while seeking new buoyant equilibrium positions and the one or more weight elements change from a state of rest to a state of motion and back to a state of rest.

4. The apparatus of claim 2, wherein said body-tensioning device comprises a body-securing harness attached to a portion of the body of the patient and constructed and arranged to resist upward movement of said floatation device and the patient within said vessel, and wherein the variations of the traction force are created by raising the level of the liquid within said vessel from a first level to a higher, second level after said body-securing harness is attached to the body of the patient and the buoyant force created by said floatation device increases as said floatation device seeks a new buoyant equilibrium position at said second level against resistance to upward movement provided by said body-securing harness.

5. The apparatus of claim 1, wherein said floatation device comprises an annulus, constructed and arranged to be worn around the chest of a patient under the patient's arms.

6. The apparatus of claim 1, wherein said floatation device comprises a neck collar, constructed and arranged to be worn around the neck of a patient.

7. The apparatus of claim 3, wherein said one or more weight elements is/are selected from the group consisting of a weighted hip belt constructed and arranged to be worn around the hips of a patient, a weighted thigh cuff constructed and arranged to be worn around a thigh of a patient, a weighted calf cuff constructed and arranged to be worn around a calf of a patient, a weighted ankle cuff constructed and arranged to be worn around an ankle of a patient, a weighted sandal constructed and arranged to be worn on a foot of a patient, and a weighted shoulder harness constructed and arranged to be worn over the shoulders of a patient.

8. The apparatus of claim 4, wherein said body-securing harness comprises a hip belt worn about the hips of a patient and secured to said vessel.

9. The apparatus of claim 8, wherein said body-securing harness further comprises tethers for securing said hip belt to said vessel.

10. The apparatus of claim 8, wherein said body-securing harness further comprises a rigid patient-securing structure secured to said vessel, said hip belt being secured to said rigid patient-securing structure.

11. The apparatus of claim 1, wherein said means for varying the level of liquid within said vessel comprises a plunger device including: a drum, a drum actuating mechanism constructed and arranged to selectively move said drum between an unsubmerged position in which said drum is not submerged in the liquid within said vessel and a submerged position in which said drum is at least partially submerged in the liquid within said vessel, wherein submersion of said drum into the liquid raises the level of the liquid within said vessel by an amount corresponding to a volume of liquid displaced by said drum.

12. The apparatus of claim 1, wherein said means for varying the level of liquid within said vessel comprises a liquid-displacing piston assembly including: a cylinder that is in fluid flow communication with said vessel and a piston movably mounted within said cylinder, wherein movement of said piston within said cylinder in a first direction draws a volume of liquid from said vessel into said cylinder to lower the level of the liquid within said vessel by an amount corresponding to the volume of liquid drawn into said cylinder, and movement of said piston within said cylinder in a second direction expels a volume of liquid from said cylinder into said vessel to raise the level of the liquid within said vessel by an amount corresponding to the volume of liquid expelled from said cylinder.

13. The apparatus of claim 1, wherein said means for varying the level of liquid within said vessel comprises a fluid bladder secured within said vessel and a pumping apparatus for pumping fluid into said fluid bladder, wherein fluid is selectively forced into said bladder by said pumping apparatus to increase the volume of said fluid bladder and thereby raise the level of the liquid within said vessel by an amount corresponding to the increase in volume of said fluid bladder, and fluid is released from said bladder to decrease the volume of said bladder to lower the level of fluid within said vessel by an amount corresponding to the decrease in volume of said fluid bladder.

14. A method for effecting traction on a spinal column of a patient, said method comprising:

placing the patient in a vessel containing liquid at a level sufficient to float at least one patient therein;

engaging a floatation device with a portion of the body of the patient for creating a buoyant force for buoyantly supporting the patient in the liquid contained in the vessel;

applying a body-tensioning force to one or more portions of the patient's body, the body-tensioning force having a component acting in a direction opposite to the buoyant force created by the floatation device; and raising and lowering the mean level of the liquid within the vessel so as to effect variations of the body-tensioning force exerted on the patient's body as the floatation device responds to variations in the level of the liquid within the vessel by seeking new buoyant equilibrium positions within the liquid for each variation in the level of the liquid within the vessel.

15. The method of claim 14, wherein the liquid within the vessel is maintained at a temperature of 95–98 deg. F.

16. The method of claim 14, wherein the floatation device engaged with a portion of the body of the patient comprises an annulus worn around the chest of a patient under the patient's arms.

17. The method of claim 14, wherein the floatation device engaged with a portion of the body of the patient comprises a neck collar worn around the neck of a patient.

18. The method of claim 14, wherein the body-tensioning force is applied with a body-tensioning device, attached to one or more portions of the patient's body, which creates a force on the patient's body having a component acting in a direction opposite to the buoyant force created by the floatation device.

19. The method of claim 18, wherein the body-tensioning device comprises one or more weight elements attached externally to one or more portions of the patients body, the one or more weight elements pulling on the patient's body in directions opposite to the buoyant force created by the floatation device, and wherein the variations of the body-tensioning force are created by inertial forces of the one or more weight elements generated as the floatation device and the patient supported thereby rise and fall with the level of the liquid within the vessel while seeking new buoyant equilibrium positions and the one or more weight elements change from a state of rest to a state of motion and back to a state of rest.

20. The method of claim 19, wherein the one or more weight elements is/are selected from the group consisting of a weighted hip belt worn around the hips of a patient, a weighted thigh cuff worn around a thigh of a patient, a weighted calf cuff worn around a calf of a patient, a weighted ankle cuff worn around an ankle of a patient, a weighted sandal worn on a foot of a patient, and a weighted shoulder harness worn over the shoulders of a patient.

21. The method of claim 18, wherein the body-tensioning device comprises a body-securing harness attached to a portion of the body of the patient for resisting upward movement of the floatation device and the patient within the vessel, and wherein the variations of the body-tensioning force are created by raising the level of the liquid within the vessel from a first level to a higher, second level after the body-securing harness is attached to the body of the patient and the buoyant force created by the floatation device increases as the floatation device seeks a new buoyant equilibrium position at the second level against resistance to upward movement provided by the body-securing harness.

22. The method of claim 21, wherein the body-securing harness includes a hip belt worn about the hips of a patient and secured to the vessel.

23. The method of claim 22, wherein the hip belt is secured to the vessel by one or more tethers connected at one end thereof to the hip belt and at an opposite end thereof to the vessel.

24. The method of claim 22, wherein the hip belt is secured to the vessel by attaching the hip belt to a rigid patient-securing structure secured to the vessel.

25. An apparatus for effecting traction on a spinal column of a patient, said apparatus comprising:

a vessel containing liquid at a level sufficient to float at least one patient therein;

a floatation device to be engaged with a portion of the body of a patient for creating a buoyant force for buoyantly supporting the patient in the liquid contained in said vessel;

a body-tensioning device constructed and arranged to be attached to one or more portions of the patient's body and to exert a tensioning force on the patient's body having a component acting in a direction opposite to the buoyant force created by said floatation device; and means for varying the level of liquid within said vessel by alternately displacing and replacing a volume of liquid within said vessel to raise and lower the mean level of the liquid within said vessel by an amount corresponding to the volume of liquid displaced and replaced so as to effect variations of the tensioning force exerted on the patient's body by said body-tensioning device as said floatation device responds to variations in the level of the liquid within the vessel by seeking new buoyant equilibrium positions within the liquid for each variation in the level of the liquid.

* * * * *